US008546323B2

(12) United States Patent
Agah

(10) Patent No.: US 8,546,323 B2
(45) Date of Patent: Oct. 1, 2013

(54) THROMBOSPONDIN-1 DERIVED PEPTIDES AND TREATMENT METHODS

(75) Inventor: Ramtin Agah, Salt Lake City, UT (US)

(73) Assignee: Ramtin Agah, Menlo Park, CA (US)

( * ) Notice: Subject to any disclaimer, the term of this patent is extended or adjusted under 35 U.S.C. 154(b) by 1296 days.

(21) Appl. No.: 11/922,791

(22) PCT Filed: Jun. 23, 2006

(86) PCT No.: PCT/US2006/024692
§ 371 (c)(1),
(2), (4) Date: Nov. 19, 2008

(87) PCT Pub. No.: WO2007/002534
PCT Pub. Date: Jan. 4, 2007

(65) Prior Publication Data

US 2009/0131314 A1 May 21, 2009

Related U.S. Application Data

(60) Provisional application No. 60/693,574, filed on Jun. 24, 2005.

(51) Int. Cl.
*A61K 38/10* (2006.01)
*C07K 7/08* (2006.01)

(52) U.S. Cl.
USPC ............................ 514/1.9; 514/21.5; 530/326

(58) Field of Classification Search
None
See application file for complete search history.

(56) References Cited

U.S. PATENT DOCUMENTS

| | | | | |
|---|---|---|---|---|
| 7,220,557 | B2 | 5/2007 | Hastings et al. | |
| 2002/0164668 | A1 * | 11/2002 | Durham et al. | 435/7.92 |
| 2003/0092900 | A1 | 5/2003 | Ruela-Arispe et al. | |
| 2003/0134784 | A1 * | 7/2003 | Raitano et al. | 514/12 |
| 2003/0166017 | A1 | 9/2003 | McCarthy | |

FOREIGN PATENT DOCUMENTS

| | | | |
|---|---|---|---|
| WO | WO-0239122 | A2 | 5/2002 |
| WO | WO 02061087 | * | 8/2002 |
| WO | WO/2004/037972 | * | 6/2004 |

OTHER PUBLICATIONS

Caplus Accession No. 2001:697649, abstract for Rosen et al., WO 2001059063, Aug. 16, 2001.*
Caplus Accession No. 2002:595012, abstract for Burmer et al., WO 2002061087, Aug. 8, 2002.*
Derwent Acc-No. 2002-000226, abstract for Gao et al. CN 1306089, Aug. 1, 2001.*
Libby, P., *Atheroma: More than Mush*, Lancet, 1996, 348 Suppl. 1: p. s4-7.
Please see attached pp. (5) for additional 42 references.

* cited by examiner

*Primary Examiner* — Christina Bradley

(57) ABSTRACT

Treatments employing the matricellular protein thrombospondin-1 (TSP-I) and related compositions are disclosed for stabilizing atherosclerotic plaque and decreasing occurrence of plaque rupture events leading to, for example, myocardial infarction, stroke, and acute limb ischemia. Various peptides, including certain synthetic peptides, related to TSP-I are also disclosed. Such peptides have utility in stabilizing plaque in various contexts, including the disease states mentioned above. Some of these peptides include one or more sequences related to active sites of TSP-I for regulating, e.g., TGF-ss1 and MMP-9 activity. Experimental data show that a representative peptide provides a beneficial effect with systemic injection of the peptide.

15 Claims, 9 Drawing Sheets

THROMBOSPONDIN-1 DERIVED PEPTIDES AND TREATMENT METHODS

CROSS REFERENCE TO RELATED APPLICATION

This application claims the benefit from U.S. Provisional Application Ser. No. 60/693,574, filed Jun. 24, 2005.

BACKGROUND OF THE INVENTION

1. Field of the Invention

The present invention relates to treatments employing the matricellular protein thrombospondin-1, TSP-1, and related compositions in stabilizing atherosclerotic plaque and thereby decreasing occurrence of plaque rupture events leading to, for example, myocardial infraction, stroke, and acute limb ischemia. Furthermore, the invention pertains to various peptides, including certain synthetic peptides for use in stabilizing plaque in various contexts, including the disease states mentioned above.

2. Description of Related Art

Atherosclerosis life-threatening complications such as acute myocardial infarction and stroke result from chronic deposition of cholesterol and its oxidized phospholipids that induce local vascular inflammation[1]. Atherosclerotic lesions form and progress in the arterial wall in part via interactions between its cellular and the extracellular matrix (ECM) constituents[1, 2]. With development of atherosclerosis there is an alteration both in the cellular and ECM constituents of the vessel wall. The ECM is recognized as a reservoir of cell binding proteins and growth factors that affect cell behavior within the atherosclerotic lesions[3, 4]. Regulation of these processes in turn may have a direct effect on cell-cell and cell-ECM interactions, which in turn may impact the phenotype of the atherosclerotic plaque as it may relate to its propensity for rupture and subsequent downstream events such as myocardial infarction and stroke.

Minor protein components of ECM, that provide specific contextual information to cells about their environment have been named 'matricellular' proteins[4]. The matricellular proteins interact with other ECM constituents, multiple specific cell surface receptors, as well as growth factors, to modulate cell-matrix interactions. These proteins modulate cell function but do not appear to contribute directly to the organization or physical properties of structures as do other ECM components such as fibrils, collagen and elastin[5]. These proteins function at the interface between extracellular matrix and the cell surface to regulate cellular behavior. Furthermore, whereas structural proteins have a key role in normal vascular development, matricellular proteins are expressed in adult vessels only at the time of injury[6]. Specifically these proteins seem to have their major function in tissue repair and act contextually to influence cell function by modulating cell-matrix interactions. As such, whereas targeted disruption of structural ECM proteins in the germline results in severe or lethal phenotypes, knockout of genes that code for matricellular proteins produces an apparently normal or subtle phenotype[7-11].

TSP-1 is a prototypical matricellular protein with multiple binding domains[3, 12]. TSP-1 is induced at the time of injury. Mice that are homozygous for a null mutation in this protein do not have significant development defects; the main phenotype in these mice are patches of acute and organizing pneumonia in the lungs. However in various disease models there are clear phenotypes ascribed to these mice[10]. For instance in wound repair models, TSP-1 deficiency is associated with alteration in inflammatory cell response and delayed wound healing. Other studies have shown that TSP-1 inhibits angiogenesis[13-19]. As such, targeted expression of TSP-1 in neoplastic cells has been of clinical interest and its modification is currently being evaluated for use in phase II clinical trails[20].

In terms of coronary heart disease recent correlational and descriptive studies suggest that TSP-1 may have a role, albeit undefined and unknown, in atherosclerosis and myocardial infarction[21, 22]. First, a case controlled genetic variation study has suggested that a missense 'mutation' in this gene is associated with increased risk of both atherosclerosis and myocardial infarction[21]. Second, pathological studies using human samples have shown TSP-1 to be present in the atherosclerotic lesion but not in the native vessel wall[23, 24]. However, at the present time, the significance of TSP-1 expression within the plaque on the atherosclerotic phenotype is unknown.

SUMMARY OF THF INVENTION

The present invention provides methods employing TSP-1 and related compositions to stabilize atherosclerotic-plaque and decrease propensity of atherosclerotic lesions to rupture—be it in any vascular bed (e.g., coronary, cerebral or peripheral limb). The invention also provides compositions employing TSP-1 and related peptides including certain synthetic peptides, related to TSP-1. Such peptides have utility in stabilizing plaque in various contexts, including the disease states such as myocardial infarction, stroke, and acute limb ischemia. Some of these peptides include one or more sequences related to active sites of TSP-1 for regulating, e.g., TGF-β1 and MMP-9 activity.

In certain embodiments, the present invention provides peptide sequences (based on TSP-1) that have been found to impact MMP-9 activation. We postulate that the mechanism for this activity is through a unique β2-integrin binding site on TSP-1 that competes with MMP-9 ability to bind leukocytes (primarily monocytes) within atherosclerotic lesions. Furthermore, in certain embodiments, the invention provides peptide sequences based on sequences within TSP-1, known to regulate TGF-β1 activity. Such sequences have application for plaque stability. Lastly we provide the sequences of various specific synthetic peptides, based on the active sites discussed above, that emulate both the TGF-β1 and MMP-9 activity of TSP-1 and its plaque stabilizing effect in vivo.

DETAIL DESCRIPTION OF THE INVENTION

Figure 1:
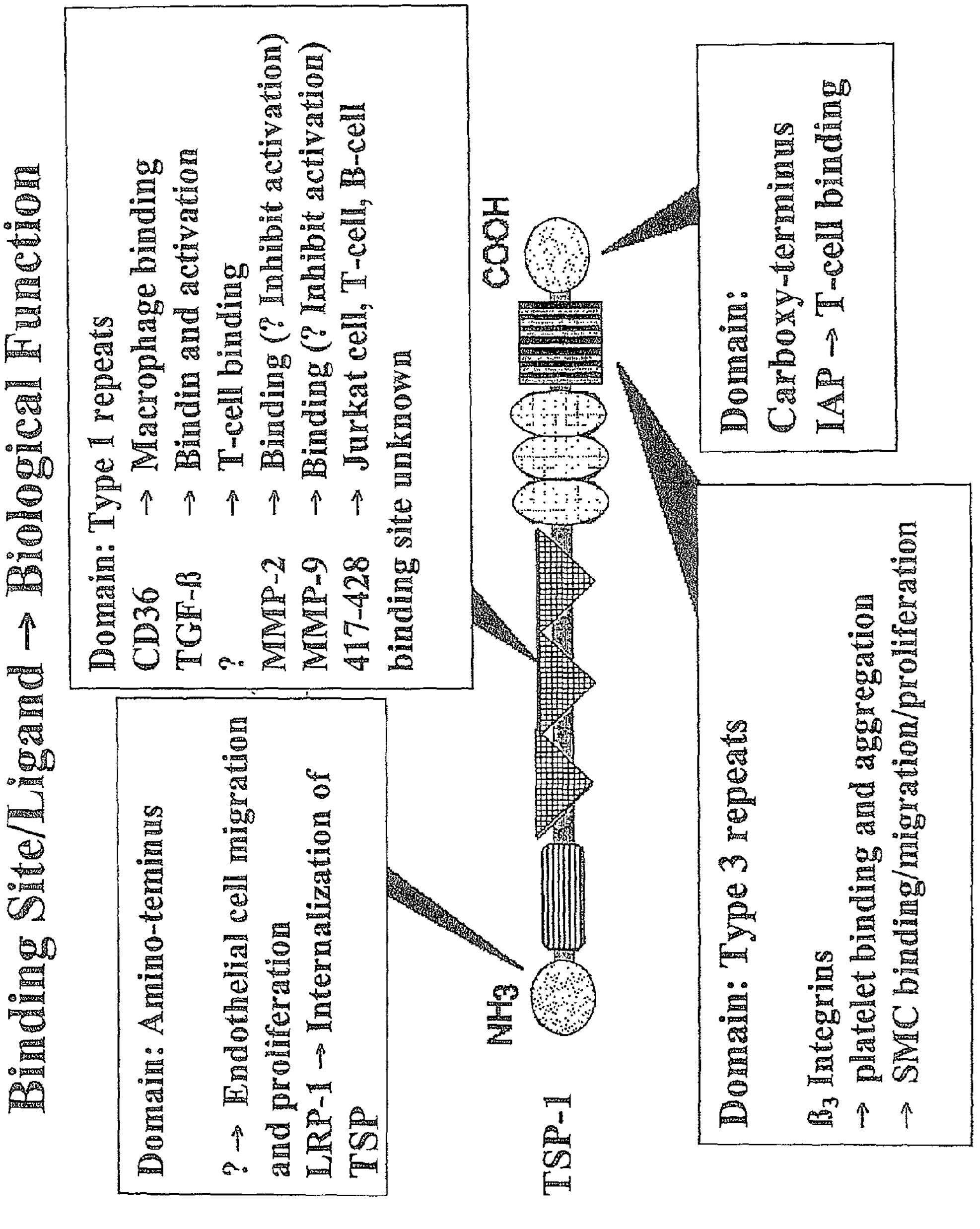
FIG. 1 shows various TSP-1 cellular and cytokine binding domains which may have direct relevance in the setting of the atherosclerotic lesions.

In order to facilitate review of the various embodiments of the invention and provide an understanding of the various elements and constituents used in making and using the present invention, the following terms used in the invention description have the following meanings.

Definitions

A method of treating a viral infection, is meant herein to include "prophylactic" treatment or "therapeutic" treatment. A "prophylactic" treatment is a treatment, administered to a subject who does not exhibit signs of a disease or who exhibits early signs of the disease for the purpose of decreasing the risk of developing pathology associated with the disease.

The term "therapeutic," as used herein, means a treatment administered to a subject who exhibits signs of pathology for the purpose of diminishing or eliminating those signs.

The term "therapeutically effective amount," as used herein means an amount of compound that is sufficient to provide a beneficial effect to the subject to which the compound is administered. A beneficial effect means stabilizing atherosclerotic plaque.

The terms "peptide," "polypeptide" and "protein," as used herein, are used interchangeably to denote a sequence polymer of at least two amino acids covalently linked by an amide bond.

The term "homologous," as used herein, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 80% identical, and preferably at least 90%, and more preferably 98%, homology to the reference peptide.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having TSP-1 peptide like characteristics. For example, certain amino acids can be substituted for other amino acids in a sequence without appreciable loss of peptide activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art J. and R. F. Doolittle 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate-(−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within .+−0.2 is preferred, those that are within .+−. 1 are particularly preferred, and those within .+−.0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide. As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); proline (−0.5.+−0.1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within .+−0.2 is preferred, those that are within .+−0.1 are particularly preferred, and those within .+−.0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of a peptide as set forth above.

TABLE 1

| Original Residue | Exemplarv Substitutions |
|---|---|
| Ala | Gly, Ser |
| Arg | Lys |
| Asn | Gln; His |
| Asp | Glu |

TABLE 1-continued

| Original Residue | Exemplarv Substitutions |
|---|---|
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed.

Amino acid residues can be added to or deleted from the TSP-1 peptides of the present invention through the use of standard molecular biological techniques without altering the functionality of the peptide. For example, terminal portions of the TSP-1 peptide can be removed to create truncated peptides, however, the truncated peptides retain the functional activities of the TSP-1 peptides of the present invention including modulating TGF-β1, or MMP-9 through protein-protein interactions and stabilizing atherosclerotic plaque.

A polypeptide of the present invention is prepared by standard techniques well known to those skilled in the art. Such techniques include, but are not limited to, isolation and purification from tissues known to contain that polypeptide, expression from cloned DNA that encodes such a polypeptide using transformed cells or use of synthetic peptide production systems.

TSP-1 Structural Domains and its Matrix Binding Partners

TSP-1 is a trimer with a chain molecular mass of 150 kda. Each subunit of the protein is made up of several structural domains[12]. These domains can broadly be defined as an amino terminal domain, a procollagen domain, type 1, type 2, and type 3 repeat sequences and a carboxyl-terminal domain [25, 26]. Each domain has been shown to be important in modifying a number of cellular functions, as shown in FIG. 1. Furthermore specific ligand binding sites have been defined for TSP-1 (FIG. 1). These include lipoprotein receptor related protein (LRP), CD36, β3 integrin, and integrin associated protein (LAP) and cytokines including TGF-β1 and PDGF[3, 12, 27, 28]. Through its multiple binding sites, TSP-1 appears to function at the cell surface to bring together membrane proteins and cytokines. In this manner TSP-1 influences the cellular phenotype including signal transduction and transcription. As each cell expresses a different repertoire of receptors, the composition of the complexes formed by TSP-1 and the respective cellular responses varies with each cell type. For instance, TSP-1 enhances smooth muscle cell migration but inhibits endothelial cell migration[29-31].

In most organ systems studied to date, a significant part of the biology of TSP-1 has been attributed to its extracellular activation of TGF-β1 [10, 13-15]. Specifically, loss of TSP-1 has been shown to decrease TGF-β1 activity and mimic the phenotype of TGF-β1 loss in the respective organ system. For instance in studies of the TSP-1 knockout mouse, loss of TSP-1 leads to localized alveolar inflammation and chronic pneumonia in similar fashion to the findings in the TGF-β1 knockout mouse[10]. Furthermore, biological complementation with short peptide fragments of TSP-1 shown to be sufficient for TGF-β1 activation (KRFK (SEQ ID NO: 2) corresponding to amino acid residues 430->433 please refer to FIG. 2) rescues this phenotype—implicating activation of TGF-β1 as the key cellular process dictating the phenotypic changes in this setting[13, 15].

TSP-1 can also regulate the activity of extracellular proteases including matrix metalloproteinases (MMPs) [32, 33]. In the setting of tumor angiogenesis, targeted expression of TSP-1 has been associated with decreased MMP-9 activity, consistent with its anti-angiogenic features. Both MMP-2 and MMP-9 have been shown to bind to TSP-1[33]. However, the binding site for MMP(s) to TSP-1 had not been defined, nor has its mechanism for regulating the activity of these proteases.

There are experimental data indicating a role for both TGF-β1 and MMP-9 in atherosclerotic plaque phenotype, including (but not limited to): matrix turnover, leukocyte recruitment and smooth muscle cell migration. Furthermore, as discussed above, TSP-1 has been shown to regulate the activity of each of these ligands in response to tissue injury.

We have determined that TSP-1 has a plaque stabilizing role in atherosclerotic plaque in mice. Furthermore we have identified the active peptide domains in TSP-1 that regulates these activities, as it relates to TGF-β1 and MMP-9. Lastly, we have designed peptides that contain peptide sequences based on these active domains, and have been able to show that a representative synthetic peptide simulates the effect of TSP-1 in vivo in mouse model of atherosclerosis.

TSP-1 Deficiency Alters the Atherosclerotic Plaque

We have been able to show that the TSP-1 matricelluar protein has plaque stabilizing effect. We generated double knockout TSP−/−ApoE−/− mice and examined the role of TSP-1 deficiency on lesion formation and composition. After 24 weeks of chow diet (3% fat) the TSP−/−ApoE−/− mice, and the ApoE−/− control mice were sacrificed. There was no significant difference in weight, total cholesterol, HDL cholesterol and triglycerides between the TSP knockout mice and the control animals.

Figure 3:
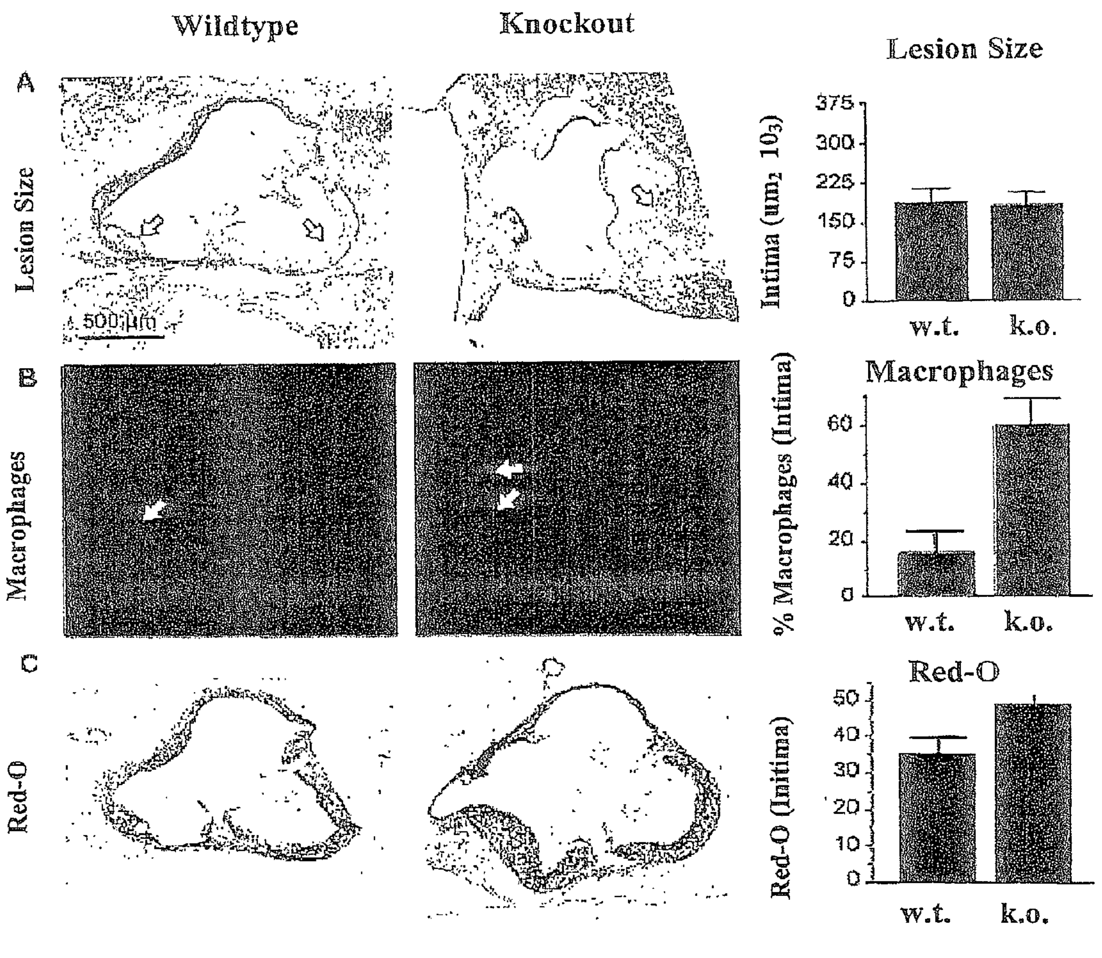
FIG. 3 shows the histological characteristics of TSP-1 deficiency on atherosclerotic lesion. (A) Hematoxylin-and-eosin-stained aortic cusp section. The bar on the right represent the lesion area (intima). No change in lesion area is detected. (B) Moma-2 antibody staining (PE conjugated representing red fluorescence) reveals there is an increase in macrophages within the aortic cusps lesion in TSP-1 deficient mouse (p<0.01). (C) Concordant with an increase in macrophages, Red-O staining reveals that there is an increase in lipid deposition within the lesion in TSP-1 deficient mouse (i.e. foam cells, p<0.05). (D) Smooth muscle cell actin antibody staining (FrrC conjugated revealing green fluorescence) . There is no staining of smooth muscle cells (smc) within the intimal lesion, and total smc content in the media is unchanged between the two groups. (E) Picosirius red polarization staining for collagen-reveals loss of collagen (decreased yellow-red staining) within the lesions in the aortic cusps (p<0.01). Note there is intense (yellow-red) staining around the cusp and valve leaflet structure in both strain of mice. But within the lesion (pointed by arrow) there is decreased staining in TSP knockout mice. (F) Verhoeff's staining for elastin reveals increased loss of elastin (black-blue staining) in the medial and intimal aspect in the areas of lesion development with TSP-1 deficiency (p<0.05).
Figure 3:
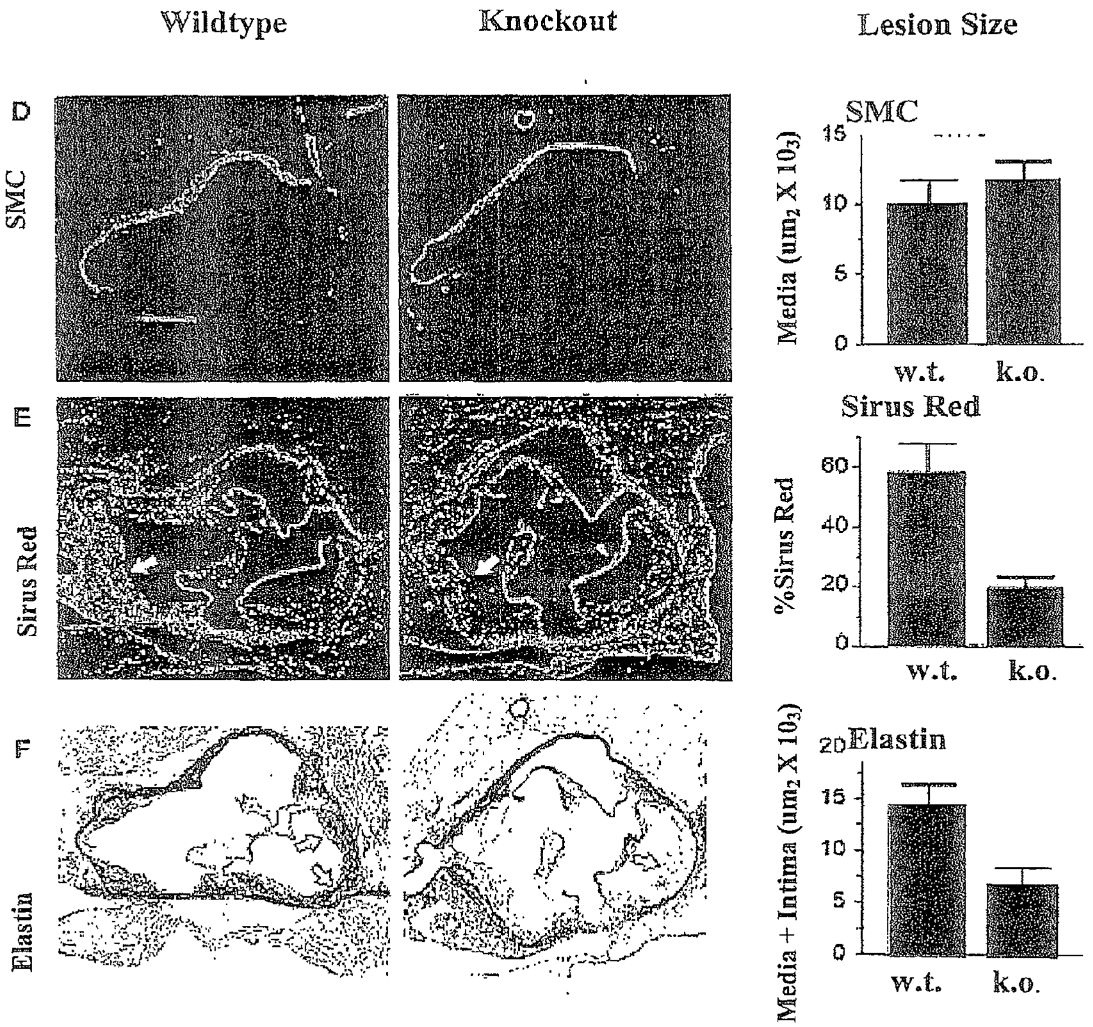

Characterization of the aortic sinus for the extent of atherosclerotic lesion using H&E staining revealed similar lesion formation in both groups (701,000 μm±95,000 μm2 for TSP knockout mice vs. 724,000 μm2±103,000 μm2 for control mice). We, performed detailed morphological evaluation of the aortic cusps for lesion composition (FIG. 3). Loss of TSP-1 had a significant influence on lesion, morphology both in the intima and the media. Specifically, in the TSP knockout mice there was (1) increased inflammation (macrophages) in the initial lesion (2) increased lipid deposition within the intimal lesions (3) decreased matrix (as measured by collagen and elastin) deposition within the lesion (4) medial ectasia with loss of media as demonstrated by decreased collagen and elastin content in the medial area in these mice and (5) no change in total, smooth muscle cell content the media. Collectively, these results suggest that the lack of TSP-1 alters the balance between inflammation and fibrosis within the plaque. This leads to on inflammatory plaque phenotype with reduced extracellular matrix content.

We postulate that the mechanism of benefit of TSP-1 in this setting is primarily (but not limited) to two things: (a) decreased activation of TGF-β1 within the atherosclerotic lesion in absence of TSP-1 (b) increased activation of MMP-9 in the absence of TSP-1.

Figure 4:
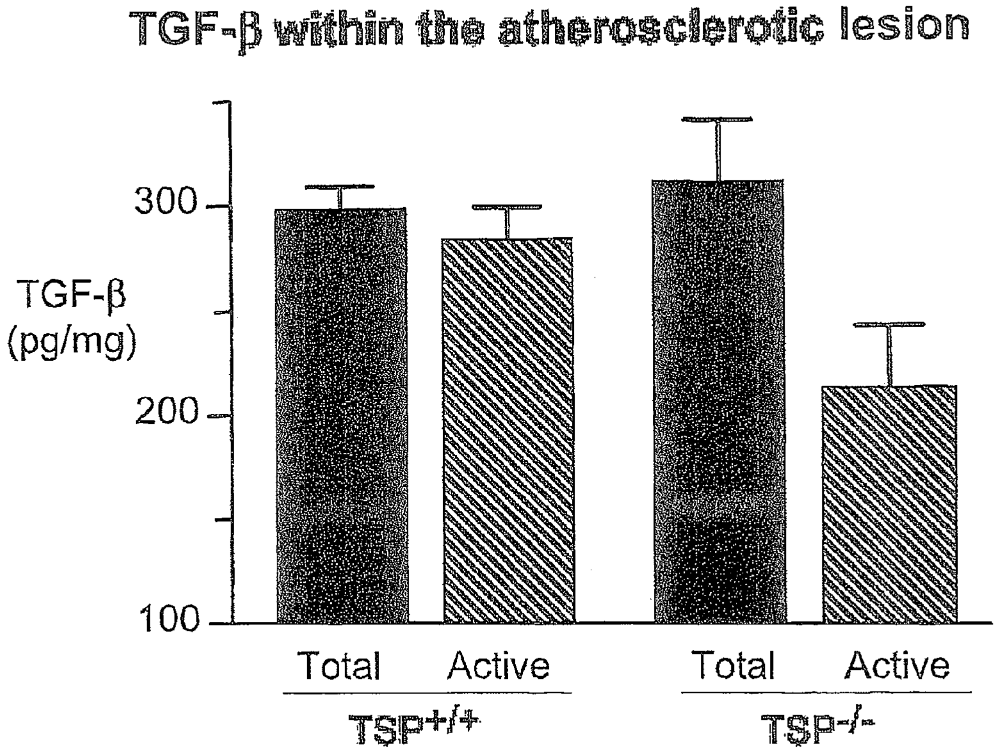
FIG. 4 shows results of a TGF-B elisa from tissue lysate of aortic arches from ApoE −/−TSP−/− (n=3 nm mice) and ApoE−/− mice (n=3 mice). There is no difference between the two group for total TGF_B1 levels, but there is a significant decrease (p<0.05) in active TGF-B1 levels within the aorta of ApoE −/−TSP−/− mice.

Activation of TGF-β1 is Decreased Within the Atherosclerotic Lesion in the TSP−/− ApoE−/− Mice As already discussed, in other studies of TSP-1 in tissue injury in vivo, the phenotypic findings in large pant have been attributed to the ability of TSP-1 to activate TGF-β1 locally at the site of injury. Furthermore, neutralization of TGF-β1 activity has been shown to increase inflammation and decrease matrix within the atherosclerotic lesion, similar to our preliminary findings in the TSP−/−ApoE−/− mice[34, 35]. Hence, we measured both total and active TGF-β1 levels in tissue from TSP−/−ApoE−/− animals. We homogenized samples from the aortic arch, an area known to be prone to atherosclerosis formation, and used the lysate in an ELISA assay. There was no change in total (latent and active) TGF-β1 level in these mice, but there was a decrease in active TGF-β1 levels (FIG. 4) in the TSP−/−ApoE−/− mice. In contrast to the result using lysate of the atherosclerotic lesions, there was no difference in systemic (serum) levels of active TGF-β1 between TSP−/−ApoE−/− and the ApoE−/− mice (225±87 pg/ml vs. 186±138 pg/ml). These data suggest that loss of TSP-1 leads to decreased TGF-β1 activation locally within the vessel-wall.

Increased Activation of MMP-9 in the TSP−/−Apo−/− Mice

Figure 5:
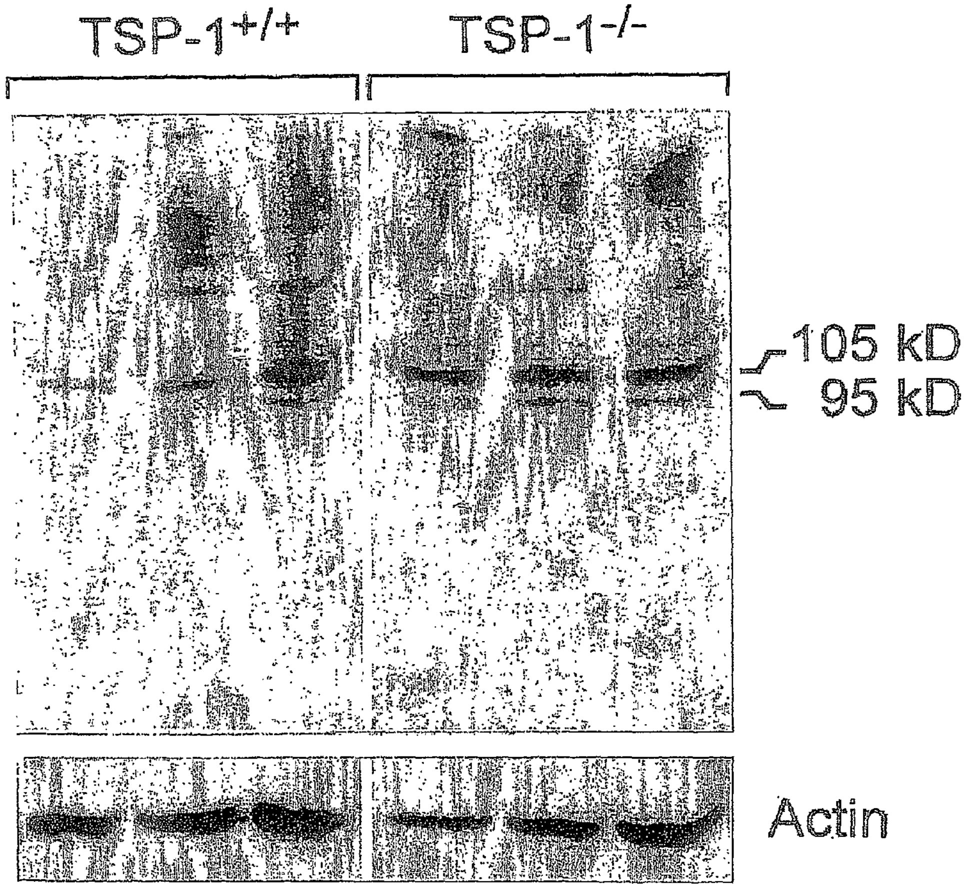
FIG. 5 shows a MMP-9 western blot from tissue lysate of aortic arches from ApoE −/−TSP−/− (n=3 mice) and ApoE−/− mice (n=3 mice). Each lane specifies on individual mouse. There is an increase in both Pro-MMP9 (105 kb) and active-MMP9 (95 kb) bands in TSP−/− mice.

Immunoprecipitation experiments, have shown that Gelatinase-B (MMP-9) binds TSP-1[33]. Furthermore, it has been shown that TSP-1 can control pro-MMP-9 conversion to the active form[32]. However the mechanism for this post-translational regulation of MMP-9 by TSP-1 has not been determined. As there is significant loss of matrix within the lesion in the TSP−/−ApoE−/− mouse (FIG. 3*e*), we examined the MMP-9 levels using tissue lysate from the aortic arch homogenate in a western blot. There was an increase in both total and active MMP-9 levels in the atherosclerotic lesion in these mice, as shown in FIG. 5.

These results indicate that loss of TSP-1 leads to increased activation of MMP-9 locally within the atherosclerotic lesions, consistent with a potential inhibitory effect of TSP-1on MMP-9 activity. The studies of MMP-9 deficiency in apoE knockout mouse have shown that the loss of MMP-9 is associated with: decreased number of macrophages, and with increased collagen synthesis[36].

As a further refinement of our findings, we set out to establish the "active" sites of TSP-1 effect on both TGF-β1 and MMP-9 activity. As we postulated that the extracellular mechanisms for TSP-1 regulation of these ligands is orchestrated through cell surface interaction within the plaque, we utilized a cell culture system using murine macrophages (RAW cells) as they are the preponderant cell type in our in vivo atherosclerotic plaque model. We identified the active sites for TSP-1 regulation of TGF-β1 activity (previously reported) and the site that impacts MMP-9 activity (determined by us).

TSP-1 Binds Macrophages Through its Putative .beta.2 Integrin Binding Motif D(D/E)(G/L)W (SEQ ID NO: 7)

Figure 2A:
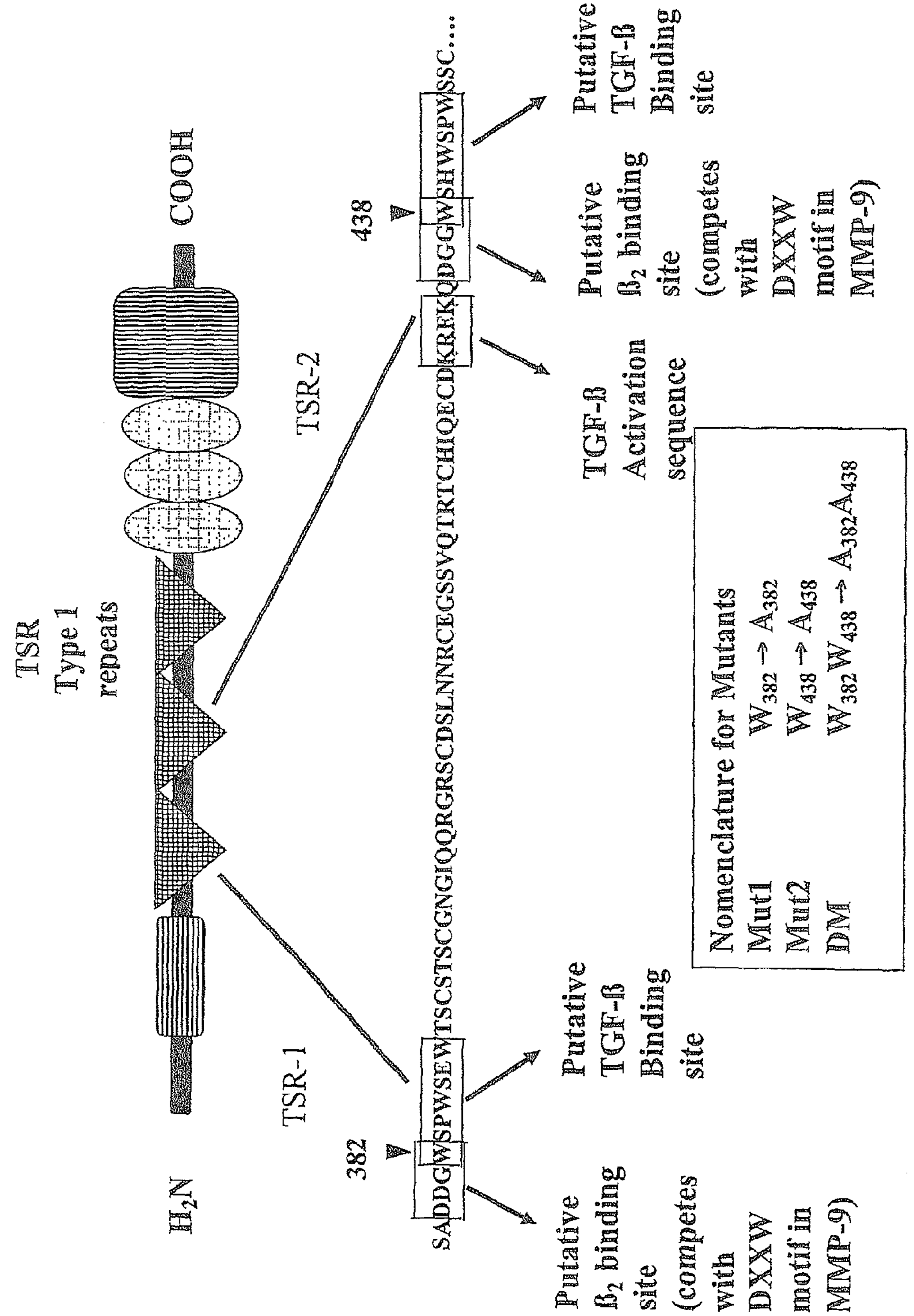
FIG. 2 shows TSR-1 and 2 binding domains in TSP-1 and the relevant mutants developed within these two domains. (A) There are two putative β2 integrin binding domain in TSR-1 and TSR-2. Note that these two binding domains are adjacent (and overlap by one amino acid) the two binding domains for TGF-β1. We have mutated the two DxGW motifs as shown in the box. (B) Using transient transfection of mouse macrophage cell lines (Raw) we see that TSP-1 decreases MMP-9 activity, $p<0.05$ (active MMP-9/total MMP-9 ELISA). This effect is abolished by TSP mutants: DM and less so by Mut1. (C) Using the same cell system, we see that TSP-1 increases TGF-β1 activity, $p<0.05$ (using the cell lysate to measure luciferase induction via a TGF-β1 promoter responsive element[39]). This affect is abolished with both TSP-1 mutants Mut1 and Mut2. In summary the DxGW motif in TSR-1 and TSR-2 appear to mediate the effects on of TSP-1 on TGF-β1 activation and MMP-9 inhibition in this cell assay system.
Figure 2B:
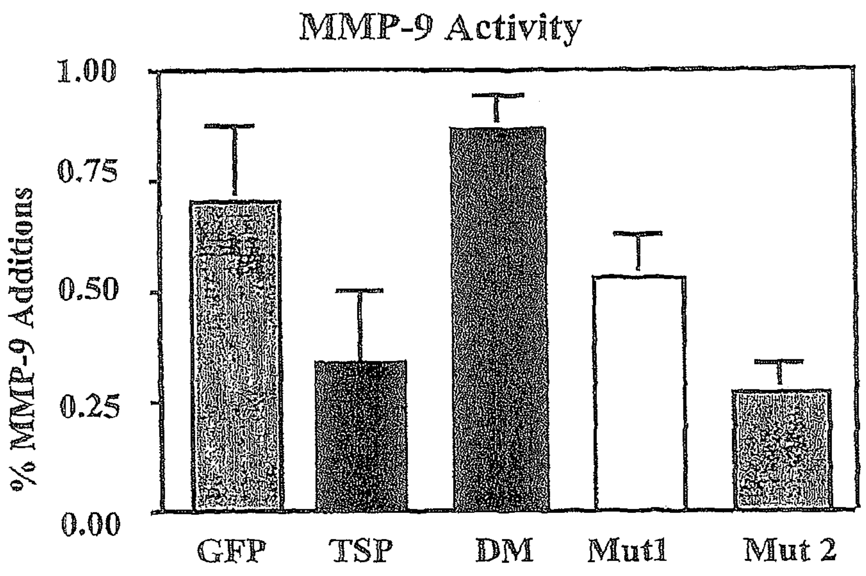
Figure 2C:
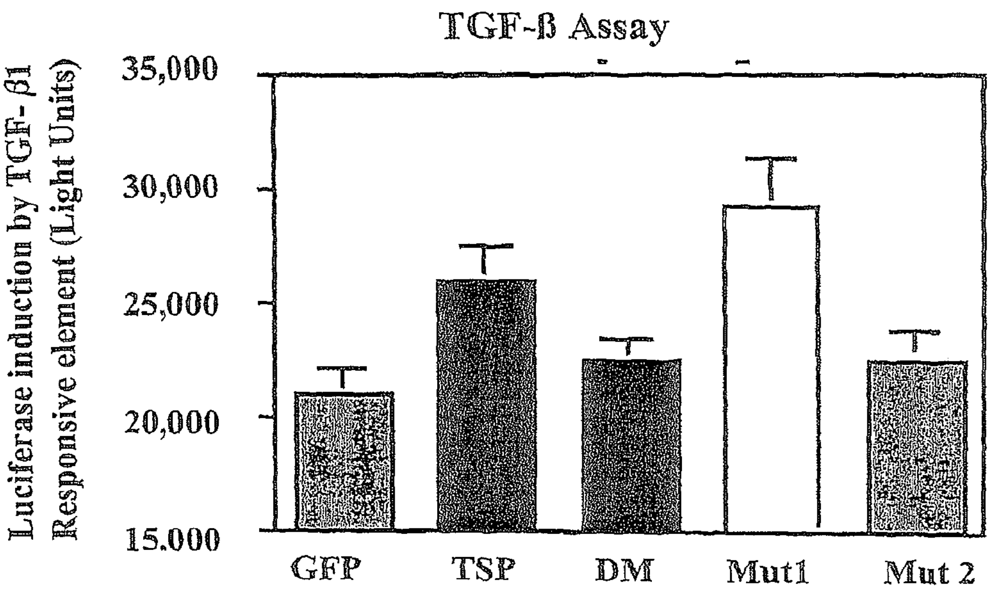
Figure 6:
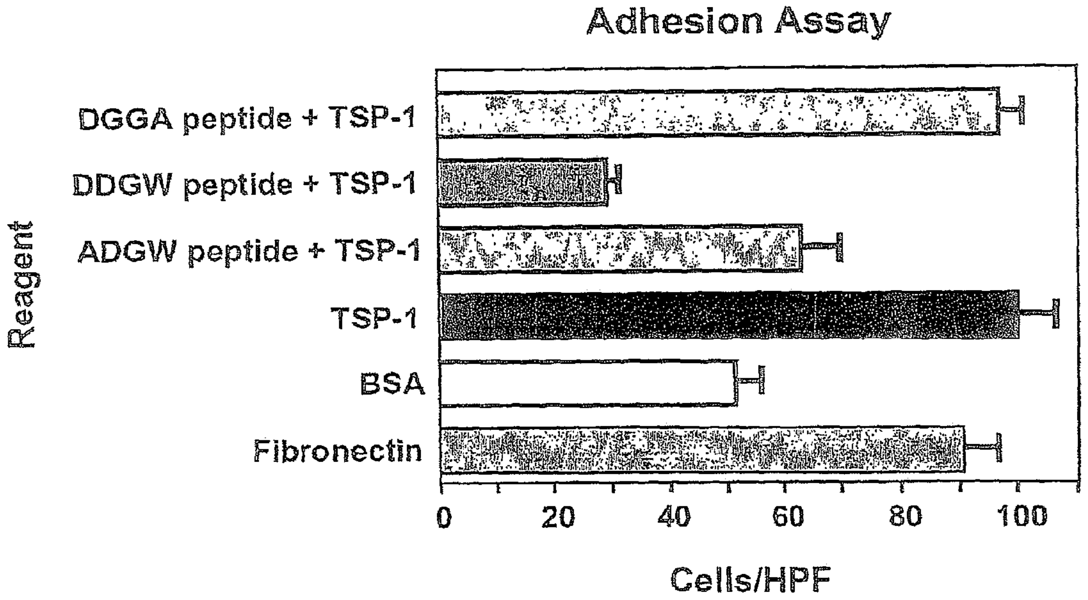
FIG. 6 shows the results of an adhesion assay wherein wells were pre-plated with TSP-1 (40 microg./ml), BSA (5%) or Fibronection (0.1 microg./ml) respectively. For the peptide experiment, the cells were mixed in suspension with respective peptide (0.01M) for 30 minutes prior to being introduced to TSP-1 wells.

TSP-1 has multiple potential binding sites for binding macrophages including CD44, IAP, and CD36 (FIG. 1). However there has been no previously established .beta.2-integrin binding motif described in TSP-1. A prior-study using phage sequence assays has reported that the peptide motif D(D/E)(G/L)W (SEQ ID NO: 7) competes with pro-MMP-9 binding to β2-integrin [40]. Through a sequence search of the complete TSP-1 peptide sequence we have determined that TSP-1 has two such putative β2 integrin binding sites: one in TSR-1-(DDGW (SEQ ID NO: 3), a perfect consensus) and another in TSR-2 (DGGW SEQ ID NO: 3), a close consensus with substitution in position 2) as shown in FIG. 2. We have used cell adhesion assay to assess binding of TSP-1 to macrophages (FIG. 6). Using this assay we have been able to show the impact of the D-Xaa-G-W (SEQ ID NO: 5) motif in TSP-1 adhesion to macrophages. Specifically, we have been able to show that peptide sequence DDGW (SEQ ID NO: 3) is sufficient to inhibit cell adhesion to TSP-1. The specificity of this competition was shown by lack of interference of macrophage binding to TSP-1 by the peptide sequence DDGA (SEQ ID NO: 4), and partial interference with the sequence ADGW (SEQ ID NO: 6).

Decreased Activation of proMMP-9 by Macrophages in the Presence of TSP-1 is Mediated Through a DDGW (SEQ ID NO: 3) Motif in TSR-1

Figure 7:
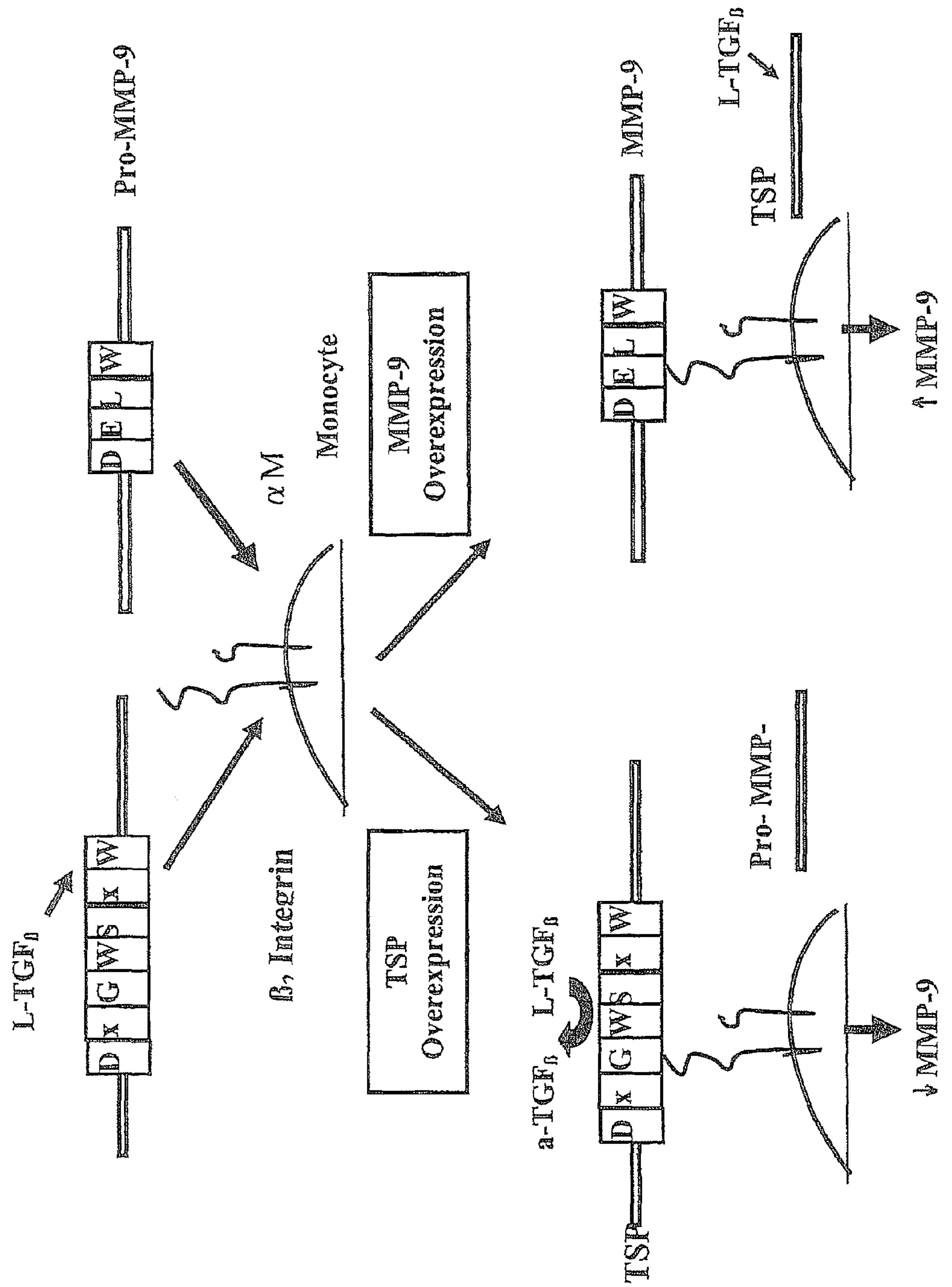
FIG. 7 illustrates the mechanism for TSP-1 and proMMP-9 competition for binding $a_M\beta2$ integrin site on Macrophages. In presence of increased TSP-1, there is increased TSP-1 binding with decreased MMP-9 activation and increased TGF-β1 activation (B). In the setting of increased proMMP-9 there is increased MMP-9 binding, with decreased TSP-1 mediated TGF-β1 activation and increased MMP-9 activation.

Little is known about the mechanism of TSP-1 regulation of MMP-9. However, proMMP-9 has been shown to bind cell surface aMβ2 and aLβ2 integrin through its D(D/E)(L/G)W (SEQ ID NO: 7) motif, leading to its activation We have shown TSP-1 binding, to macrophages through the same motif and we postulate one potential mechanism for TSP-1 inhibition, of MMP-9 activity may involve displacement of pro-MMP-9 from cell surface (FIG. 7) by competition for binding. To test this hypothesis we generated various mutants of TSP-1 involving either or both potential β2-intergin binding motif in TSP-1 (FIG. 2). Transient transfection of RAW cells (macrophage cell line) with TSP-1 decreased conversion of pro-MPP-9 to the active form. This effect was reversed by mutation of the TSR-1 motif but less so with mutation of the TSR-2 motif. These results demonstrate the importance of DxGW (SEQ ID NO: 5) motif, especially in TSR-1, in TSP-1 inhibition of MMP-9 activation likely through competing with pro-MP9 binding to β2-integrin.

Activation of TGF-β1 by TSP-1 is Abrogated by a Mutation in WSPW (SEQ ID NO: 9) Motif in TSR-2

The WSxW (SEQ ID NO: 8) motif in TSP-1 has previously been shown to be important for TGF-.beta.1 activation. To test this hypothesis we undertook tissue culture experiments to demonstrate that TSP-1 indeed activates TGF-β1 in presence of activated macrophages. Furthermore, using our mutants we have observed that WSPW (SEQ ID NO: 9) motif in TSR-2 is primarily responsible for TGF-β1 activation by TSP-1.

Based on these data we postulate that the DDGW (SEQ ID NO: 3) motif within TSR-1 binds aMβ2-integrins on leukocytes and through this binding impacts cell surface mediated MMP-9, activity. Furthermore the WSPW (SEQ IN NO: 9) motif in TSR-2 is important for TGF-β1 activation.

As such we have identified the two active sites in TSP-1 important for both (1) decreasing MMP-9 activity (2) and activating TGF-β1. Using this knowledge, many peptides having plaque stabilizing properties can be designed and synthesized. We designed and synthesized a representative synthetic sequence combining these two active sites: KRFKQDDGWSPWSEW (SEQ ID NO: 10). We postulated that this peptide fragment, combining these two key activity sites for TSP-1 function, may exert the same beneficial effects on plaque stability in vivo as the whole protein. To test this, first we tested and confirmed the ability of this peptide to both (1) activate TGF-β1 and (b) inhibit activation of MMP-9 in tissue culture.

Next we injected this peptide in TSP−/− mice using alzet infusion pump at a concentration of 8-25 μg per day for 5 weeks and were able to show that this peptide was sufficient to rescue the phenotype of the TSP−/− ApoE−/− mice (decrease macrophages and increase matrix within the lesion). Furthermore, in apoE−/− mice, the infusion of the peptide also had a beneficial effect, proving the ability of the compound to stabilize plaque even in presence of endogenous TSP-1. In other words, in comparison to the untreated TSP−/− mice, there was (1) decreased inflammation (macrophages) in the intimal lesion, (2) decreased lipid deposition within the intimal lesions, and (3) increased matrix (as measured by collagen and elastin) deposition within the lesion.

In conclusion, our results demonstrate that TSP-1 (1) can have a beneficial effect on stabilizing atherosclerotic plaque and (2) at least one synthetic peptide combining the active sites of TSP-1 important for its regulation of MMP-9 and TGF-β1 is able to stabilize atherosclerotic plaque in mouse model of the disease.

Generally, "stabilized plaque" is evidenced by limited inflammation at the site of the lesion and/or significant fibrosis within the plaque. These features may be observed by a comparison a TSP-1 deficient control system such as the TSP−/− mice described above. Generally, stabilized plaque may be identified by a comparison of fibrosis and inflammation in treated and untreated animals. The balance between fibrosis and inflammation within the plaque has been a well accepted surrogate marker for propensity of plaque to rupture in multiple different animal models[41-43].

Additional Embodiments

Peptide Sequences

This invention provides various novel peptides. These may include one or more of various binding domains and activation sequences, and homologs thereof.

Peptides having subsequences (domains) that bind with or activate TGF-β and/or MMP-9.

Class 1. Sequences that correspond to a domain found on TSP-1 and/or MMP-9 for binding to β2-integrin, particularly aMβ2 and aLβ2 integrin. Such sequences provide a domain for binding with the site on β2-integrin where MMP-9 normally binds. Alternatively, the domain may provide a site for binding to some other location on β2-integrin, but in so doing blocks native MMP-9 from binding with β2-integrin.

Various sequences may comprise such domain. Some such sequences are found on native MMP-9. Other such sequences are found on TSP-1, particularly in the type 1 repeat domain. In one example, the domain comprises a four amino acid sequence represented as D-Xaa-(L/G)-W (SEQ ID NO: 11) or (D/E)-(D/E)-(G/L)-W (SEQ ID NO: 2) or D-(D/E)-(L/G)-W (SEQ ID NO: 7). Specific examples of such sequence include DDGW (SEQ ID NO: 3), DGGW, (SEQ ID NO: 4) and DELW (SEQ ID NO: 13).

Class 2. Another domain that may be provided in the novel peptide sequences of this invention binds with native TGF-β. Certain of these sequences are found in the type 1 repeat domain of TSP-1.

In a specific example, such sequence comprises W-S-Xaa1-W-S-Xaa2-W (SEQ ID NO: 14). In a specific example, Xaa1 is P or H and Xaa2 is E or P. A very specific example of such peptide is WSPWSEW.

Class 3. Yet another sequence that may be employed in novel peptides of this invention comprises an amino acid sequence that activates latent forms of TGF-β. Some such sequences are found in the type 1 repeat domain of TSP-1.

Examples of such sequences include KRFK (SEQ ID NO: 2) and KRFKQ (SEQ ID NO: 15).

Various combinations of the three classes of sequences/domains described above may be employed in novel peptides or combinations of peptides in accordance with embodiments of this invention.

In the first example, the peptide (or composition comprising a combination of peptides) includes only a sequence from class 1 described above; i.e., the sequence corresponding to a β2-integrin binding domain. Such peptides would not include additional sequences from classes 2 and/or 3 described above.

In the second example, the peptide (or composition comprising a combination of peptides) includes sequences from classes 1 and 2 described above. In another words, a single peptide sequence (or composition comprising a combination of peptides) includes both a sub sequence corresponding to a β2-integrin binding domain and a different subsequence that binds with TGF-β.

A third type of peptide (or composition comprising a combination of peptides) of this invention includes both sequences from classes 1 and 3 described above. In other words, such peptides (or composition comprising a combination of peptides) include both a subsequence that corresponds to a β2 integrin-binding domain and another subsequence that activates TGF-β.

And yet another class of peptides (or composition comprising a combination of peptides) of this invention, the peptides include a combination of each of classes 1, 2, and 3 described above. Such peptides (or composition comprising a combination of peptides) will include sequences corresponding to a β2-integrin binding domain, a binding site for TGF-β, and an activation sequence for converting latent TGF-β to active TGF-β.

Note that in any peptides employing two or more binding or activation domains, some overlap between the individual subsequences or domains is permitted. For example, one or more of the amino acids in the peptide can be shared by two or more of the binding or activation sites. In a specific example involving both a β2-integrin binding domain and a TGF-β binding domain, a peptide of this invention may have the sequence DGGWSPWSEW (SEQ ID NO: 16, where the first W (tryptophan) is shared by the two subsequences.

As indicated, a specific peptide of this invention that has been confirmed to be active in stabilizing plaque has the sequence KRFKQDDGWSPWSEW (SEQ ID NO: 10). Certain of the residues in a sequence are more important than others for preserving activity. Thus, variations of this sequence will preserve activity. Given that the sequence is relatively short, various insertions, deletions, substitutions and extensions will be easily identifiable by those of skill in the art without undue experimentation.

For example, various substitutions may be employed for individual amino acids within the sequence. Preferably, such substitutions employ amino acids having generally the same size and/or chemical properties as the amino acids in the base sequence, KRFKQDDGWSPWSEW (SEQ ID NO: 10).

Stated in one general sense, the peptide sequence has the form Xaa1-Xaa2-Xaa3-Xaa4-Xaa5-Xaa6-Xaa7-Xaa8-Xaa9-Xaa10-Xaa11-Xaa12-Xaa13-Xaa14-Xaa15.

Xaa1, Xaa2, and Xaa4 are preferably basic, non-cyclic amino acids. Examples include R and K.

Xaa3, Xaa9, Xaa11, Xaa12, and Xaa15 are preferably neutral, non-polar, large, and cyclic amino acids. These include F, W, and possibly P.

Xaa5 is preferably a neutral, polar, large, and non-cyclic amino acid. Examples include T, N, and Q.

Xaa6, Xaa7, and Xaa14 are preferably acidic amino acids. Specific examples of; natural occurring amino acids in this class are D and E.

Finally, Xaa8, Xaa10, and Xaa13 are preferably neutral, polar, and small. Naturally occurring examples of such amino acids are G, S, and C.

In one specific embodiment, Xaa2 is R. In another specific embodiment, Xaa6 is D. In another specific embodiment, Xaa7 is D. In another specific embodiment, Xaa9 is W. In another specific embodiment, Xaa12 is W. And yet another specific embodiment, Xaa15 is W.

In yet another specific embodiment, Xaa2 is R, Xaa7 is D, and Xaa9 is W.

Note that the peptides of this invention are not limited to residues comprising the 20 naturally occurring amino acids. Certain commonly encountered non-natural amino acids, such as desamino Tyrosine (des Tyr), agmatine (Agm), n-formyl tryptophan (f-Trp), alpha-aminoisobutyric acid (Aib), and sarcosine (Sar), statine, ornithine (Orn), homolysine, homoserine, homoarginine, norleucine (NHe), norvaline may also be incorporated into the compounds of the invention.

Peptides within the scope of the present invention can be obtained by modifying the disclosed sequences in other ways, while preserving the activity of the compounds thus obtained. For example, while the amino acids of these compounds are normally in the natural L optical isomer form, one or more may be replaced with the optical isomer D form, or a D,L-racemic mixture can be provided in the molecules comprising the peptide. Additionally, a disulfide linkage may be present or absent in the compounds of the invention, as long as activity is maintained.

Amino acid residues contained within the peptides, and particularly at the carboxy- or amino-terminus, can also be modified by methylation, amidation, acetylation or substitution with other chemical groups which can, for example, change the circulating half-life, resistance to proteases and solubility of the compounds without adversely affecting their activity.

Any of the above peptides preferably comprise at least 7 amino acid residues. In other embodiments the peptides comprise between about 7 and 25 residues, between about 7 and 20 residues, between about 7 and 14 residues, between about 10 and 12 residues, between about 10 and 25 residues, between about, 15 and 25 residues, and between about 15 and 20 residues. The peptides of the invention comprise 7, 8, 9, 10, 11, 12, 13, 14, 15, 16, 17, 18, 19, 20, 21, 22, 23, 24, or 25 amino acid residues. The basic scaffold defining peptides of this invention is preferably designed so that one or more of the binding and activation sequences described above (classes 1, 2, and 3) are exposed for interaction with β2-integrin and/or TGF-β, as appropriate.

The compounds of the invention can be homopolymerized to themselves (i.e., (peptide)n) or, heteropolymerized to one another (i.e., (peptide 1-peptide 2). The compounds can also be cyclized through disulfide or other means. The compounds can also be conjugated to biocompatible molecules such as, for example, fatty acids and/or polyethylene glycol (PEG).

Peptides within the scope of the present invention can be synthesized chemically by means well known in the art such as, e.g., solid phase peptide synthesis. In other embodiments, selected compounds of the present invention can be produced by expression of recombinant DNA constructs prepared in accordance with well-known methods.

Conveniently, compounds may be synthesized using manual techniques or automatically employing, for example, various products available from Applied Biosystems (Foster City, Calif.), following the instructions provided in the instruction manual supplied by the manufacturer. It will be readily appreciated by those having ordinary skill in the art of peptide synthesis that the intermediates which are constructed in accordance with the present disclosure during the course of synthesizing the present compounds are themselves useful compounds and are thus within the scope of the invention.

Methods of Treatment

As indicated above, embodiments of the invention pertain to methods of treatment with TSP-1, portions thereof, or related peptides such as those identified herein above. Generally, TSP-1 and the peptides of the invention are administered to stabilize plaque on artery walls. Thus, they may be employed in methods of stabilizing plaque in diseased animals. This should be distinguished from methods of treating atherosclerosis.

In certain embodiments, the novel peptides of this invention may be administered to effect results other than plaque stabilization. For example, synthetic peptides having the motifs identified in Class 1 above (e.g., D-Xaa-(L/G)-W-containing peptides such as DDGW, DGGW, and DELW) may be employed to impact MMP-9 activity in vivo. Thus, such peptides may be employed to treat cancer and angiogenesis, for example. In certain embodiments, synthetic peptides having the D-Xaa(L/G)-W motif and used in vivo treatments comprise at least 7 amino acid residues, more preferably between about 7 and 20 residues, and, in a specific embodiment, comprises between about 10 and 15 residues.

The present invention provides compositions containing an effective amount of TSP-1 and peptides of the present invention, including the nontoxic addition salts, amides and esters thereof, which may, alone, serve to provide the above-recited plaque stabilizing benefits. Such compositions can also be provided together with physiologically tolerable liquid, gel or solid diluents, adjuvants and excipients.

These compositions can be administered to animals for veterinary use, such as with domestic animals, and clinical use in humans in a manner similar to other therapeutic agents. In general, the dosage required for therapeutic efficacy will range from about 1 μg to 300 mg/kg, more usually 10 μg to 30 mg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides: such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%-95% of active ingredient, preferably 25%-70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

CONCLUSION

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the specific embodiments presented in the above description, but should instead be determined with reference to the full scope of equivalents to which such embodiments are entitled. All publications mentioned herein are cited for the purpose of describing and disclosing biological mechanisms, therapeutics, methodologies and concepts that may be used in connection with the present invention. Nothing herein is to be construed as an admission that these references are prior art in relation to the inventions described herein. Unless otherwise indicated, each reference presented herein is incorporated by reference in its entirety for all purposes.

REFERENCES

The entire disclosure of each of the following references is incorporated herein by reference.

1. Libby, P., Atheroma: more than mush. Lancet, 1-348 Suppl 1: p. s4-7.
2. Ross, R., Atherosclerosis—an inflammatory disease. N Engl J Med, 1999. 340(2): p. 115-26.
3. Bornstein, P., Thrombospondins as matricellular modulators of cell function. J Clin Invest, 2001. 107(8): p. 929-34.
4. Sage, E. H., Regulation of interactions between cells and extracellular matrix: a command performance on several stages. J Clin Invest, 2001. 107(7): p. 781-3.
5. Murphy-Ullrich, J. E., The de-adhesive activity of matricellular proteins: is intermediate cell adhesion an adaptive state? J Clin Invest, 2001. 107(7): p. 785-90.
6. Elzie, C. A. and J. E. Murphy-Ullrich, The N terminus of thrombospondin: the domain stands apart. Int J Biochem Cell Biol, 2004. 36(6): p. 1090-101.
7. Li, D. Y., G. Faury, D. G. Taylor, E. C. Davis, W L Boyle, R. P. Mecham, P. Stenzel, B. Boak and M. T. Keating, Novel arterial pathology in mice and humans hemizygous for elastin. J Clin Invest, 1998. 102(10): p. 1783-7.
8. Aszodi, A., D. Chan, E. Hunziker, J. F. Bateman, and R. Fassler, Collagen II is essential for the removal of the notochord and the formation of intervertebral discs. J Cell Biol, 1998. 143(5): p. 1399-412.

9. Forsberg, B., E. Hirsch, L. Frohlich, M. Meyer, P. Ekblom, A. Aszodi, S. Werner, and R. Fassler, Skin wounds and severed nerves heal normally in mice lacking tenascin-C. Proc Natl Acad Sci U S A, 1996. 93(13): p. 6594-9.
10. Lawler, J., M. Sunday, V. Thibert, M. Duquette, B L. George, F L Rayburn, and R. O. Hynes, Thrombospondin-1 is required for normal murine pulmonary homeostasis and its absence causes pneumonia. J Clin Invest, 1998. 101(5): p. 982-92.
11. Kyriakides, T. R., J. W. Tam, and P. Bornstein, Accelerated wound healing in mice with a disruption of the thrombospondin 2 gene. J Invest Dermatol, 1999. 113(5): p. 782-7.
12. Adams, J. C. and J. Lawler, The thrombospondins. Int J Biochem Cell Biol, 2004. 36(6): p. 961-8.
13. Crawford, S. E., V. Stellmach, J. E. Murphy-Ulirich, S. M. Ribeiro, J. Lawler, R. O. Hynes, G. P. Boivin, and N. Bouck, Thrombospondin-1 is a major activator of TGF-beta1 in vivo. Cell, 1998. 93(7): p. 1159-70.
14. Agah, A., T. R. Kyriakides, J. Lawler, and P. Bornstein, The lack of thrombospondin-1 (TSP1) dictates the course of wound healing in double-TSP1/TSP2-null mice. Am J Pathol, 2002. 161(3): p. 831-9.
15. Yee, K. O., M. Streit, T. Hawighorst, M. Detmar, and J. Lawler, Expression of the type-1 repeats of thrombospondin-1 inhibits tumor growth through activation of transforming growth factor-beta. Am J Pathol, 2004. 165(2): p. 541-52.
16. Miao, W. M., W. L. Seng, M. Duquette, P. Lawler, C. Laus, and J. Lawle r, Thrombospondin-1 type 1 repeat recombinant proteins inhibit tumor growth through transforming growth factor-beta-dependent and independent mechanisms. Cancer Res, 2001. 61(21): p. 7830-9.
17. Yano, K., H. Oura, and M. Detmar, Targeted overexpression of the angiogenesis inhibitor thrombospondin-1 in the epidermis of transgenic mice prevents ultraviolet-B-induced angiogenesis and cutaneous photo-damage. J Invest Dermatol, 2002. 118(5): p. 800-5.
18. Sirnantov, R., M. Febbraio, R. Crombie, A. S. Asch, R. L. Nachman, and R. L. Silverstein, Histidine-rich glycoprotein inhibits the antiangiogenic effect of thrombospondin-1. J Clin Invest, 2001. 107(1): p. 45-52.
19. Bornstein, P., A. Agah, and T. R., Kyriakides, The role of thrombospondins 1 and 2 in the regulation of cell-matrix interactions, collagen fibril formation, and the response to injury. Int J Biochem Cell Biol, 2004. 36(6): p. 1115-25.
20. Lawler, J. and M. Detmar, Tumor progression: the effects of thrombospondin-1 and -2. Int J Biochem Cell Biol, 2004. 36(6): p. 1038-45.
21. Topol, E. J., J. McCarthy, S. Gabriel, D. J. Moliterno, W. J. Rogers, L. K. Newby, M. Freedman, J. Metivier, R. Cannata, C. J. O'Donnell, K. Kottke-Marchant, G. Murugesan, E. F. Plow, O. Stenina, and G. Q. Daley, Single nucleotide polymorphisms in multiple novel thrombospondin genes may be associated with familial premature myocardial infarction. Circulation, 2001. 104(22): p. 2641-4.
22. Stenina, O. I., T. V. Byzova, J. C. Adams, J. J. McCarthy, E. J. Topol, and E. F. Plow, Coronary artery disease and the thrombospondin single nucleotide polymorphisms. Int J Biochem Cell Biol, 2004. 36(6): p. 1013-30.
23. Raines, E. W., The extracellular matrix can regulate vascular cell migration, proliferation, and survival: relationships to vascular disease. Int J Exp Pathol, 2000. 81(3): p. 173-82.
24. Roth, J. J., V. Gahtan, J. L. Brown, C. Gerhard, V. K. Swami, V. L. Rothman, T. N. Tulenko, and G. P. Tuszynski, Thrombospondin-1 is elevated with both initial hyperplasia and hypercholesterolemia. J Surg Res, 1998. 74(1): p. 11-6.
25. Lawler, J., The functions of thrombospondin-1 and -2. Curr Opin Cell Biol, 2000. 12(5): p. 634-40.
26. Chen, H., M. E. Herndon, and J. Lawler, The cell biology of thrombospondin-1. Matrix Biol, 2000. 19(7): p. 597-614.
27. Majack R. A., S. C. Cook, and P. Bornstein, Control of smooth muscle cell growth by components of the extracellular matrix: autocrine role for thrombospondin. Proc Natl Acad Sci USA, 1986. 83(23): p. 9050-4.
28. Schultz-Cherry, S., S. Ribeiro, L. Gentry, and J. E. Murphy-Ullrich, Thrombospondin binds and activates the small and large forms of latent transforming growth factor-beta in a chemically defined system. J Biol Chem, 1994. 269(43): p. 26775-82.
29. Fischer, J. W., M. Stoll, A. W. Hahn, and T. Unger, Differential regulation of thrombospondin-1 and fibronectin by angiotensin II receptor subtypes in culture endothelial cells. Cardiovasc Res, 2001. 51(4): p. 784-91.
30. Lymn, J. S., M. K. Patel, G. F. Clunn, S. J. Rao, K. L. Gallagher, and AD. Hughes, Thrombospondin-1 differentially induces chemotaxis and DNA synthesis of human venous smooth muscle cells at the receptor-binding level. J Cell Sci, 2002. 115(Pt 22): p. 4353-60.
31. Patel, M. K., J. S. Lymn, G. F. Clunn, and A. D. Hughes, Thrombospondin-1 is a potent mitogen and chemoattractant for human vascular smooth muscle cells. Arterioscler Thromb Vasc Biol, 1997. 17(10): p. 2107-14.
32. Rodriguez-Manzaneque, J. C., T. F. Lane, M. A. Ortega, R. O. Hynes, J. Lawler, and Mi. Iruela-Arispe, Thrombospondin-1 suppresses spontaneous tumor growth and inhibits activation of matrix metalloproteinase-9 and mobilization of vascular endothelial growth factor. Proc Natl Acad Sci USA, 2001. 98(22): p. 12485-90.
33. Bein, K. and M. Simons, Thrombospondin type 1 repeats interact with matrix metalloproteinase 2. Regulation of metalloproteinase activity. J Biol Chem, 2000. 275(41): p. 32167-73.
34. Lutgens, E., M. Gijbels, M. Smook, P. Heeringa, P. Gotwals, V. E. Koteliansky, and M. J. Daemen, Transforming growth factor-beta mediates balance between inflammation and fibrosis during plaque progression. Arterioscler Thromb Vasc Biol, 2002. 22(6): p. 975-82.
35. Mallat, Z, A. Gojova, C. Marchiol-Fournigault, B. Esposito, C. Kamate, R Merval, D. Fradelizi, and A. Tedgui, Inhibition of transforming growth factorbeta signaling accelerates atherosclerosis and induces an unstable plaque phenotype in mice. Circ Res, 2001. 89(10): p. 930-4.
36. Luttun A., E. Lutgens, A. Manderveld, K. Maris, D. Collen, P. Carmeliet, and L. Moons, Loss of matrix metalloproteinase-9 or matrix metalloproteinase-12 protects apolipoprotein E-deficient mice against atherosclerotic media destruction but differentially affects plaque growth. Circulation, 2004. 109(11): p. 1408-14.
37. Stefanidakis, M., M. Bjorklund, E. Ihanus, C. G. Gahmberg, and E. Koivumen, Identification of a negatively charged peptide motif within the catalytic domain of progelatinases that mediates binding to leukocyte beta 2 integrins. J Biol Chem 2003. 278(36): p. 34674-84.
38. Stefanidakis, M., T. Ruohtula, N. Borregaard, C. G. Gahmberg, and E. Koivunen, Intracellular and cell surface localization of a complex between alphaMbeta2 integrin and promatrix metalloproteinase-9 progelatinase in neutrophils. J Immunol, 2004. 172(11): p. 7060-8.

39. Wrana, J. L., L. Attisano, J. Carcamo, A. Zentella, J. Doody, M. Laiho, X. F. Wang, and J. Massague, TGF beta signals through a heteromeric protein kinase receptor complex. Cell, 1992. 71(6): p. 1003-14.
40. Stefanidakis, M., M. Bjorklund, E. Ihanus, C. G. Gahmberg, and E. Koivunen, Identification of a negatively charged peptide motif within the catalytic domain of progelatinases that mediates binding to leukocyte beta 2 integrins. J Biol Chem, 2003. 278(36): p. 34674-84.
41. Libby, P., Atheroma: more than mush. Lancet, 1996. 348 Suppl 1: p. s4-7.
42. Ross, R., Atherosclerosis—an inflammatory disease. N Engl J Med, 1999. 340(2): p. 115-26.
43. Falk E., P. K. Shah, and V. Fuster, Coronary plaque disruption. Circulation, 1995. 92(3): p. 657-71.

What is claimed is:

1. A peptide comprising the sequence

Xaa1-Xaa2-Xaa3-Xaa4-Xaa5-Xaa6-Xaa7 Xaa8-Xaa9-Xaa10-Xaa11-Xaa12-Xaa13-Xaa14-Xaa15 wherein Xaa1, Xaa2, and Xaa4 are basic, non-cyclic amino acids independently selected from the group consisting of Arg and Lys;

Xaa3, Xaa9, Xaa11, Xaa12, and Xaa15 are neutral, non-polar, large, and cyclic amino acids independently selected from the group consisting of Phe, Trp, and Pro;

Xaa5 is a neutral, polar, large, and non-cyclic amino acid selected from the group consisting of Thr, Asn, and Gln;

Xaa6, Xaa7, and Xaa14 are acidic amino acids independently selected from the group consisting of Asp and Glu; and Xaa8, Xaa10, and Xaa13 are neutral, polar, and small amino acids independently selected from the group consisting of Gly, Ser, and Cys.

2. The peptide of claim 1 wherein the peptide consists of 15-25 amino acids.

3. The peptide of claim 1 wherein the peptide consists of 15-20 amino acids.

4. The peptide of claim 1 wherein Xaa2 is Arg.

5. The peptide of claim 1 wherein Xaa6 is Asp.

6. The peptide of claim 1, wherein Xaa7 is Asp.

7. The peptide of claim 1, wherein Xaa9 is Trp.

8. The peptide of claim 1, wherein Xaa12 is Trp.

9. The peptide of claim 1, wherein Xaa15 is Trp.

10. The peptide of claim 1, wherein Xaa2 is Arg, Xaa7 is Asp, and Xaa9 is Trp.

11. The peptide of claim 1, consisting of 15 to 25 amino acids and wherein Xaa1-Xaa2-Xaa3-Xaa4-Xaa5-Xaa6-Xaa7 Xaa8-Xaa9-Xaa10-Xaa11-Xaa12-Xaa13-Xaa14-Xaa15 is Lys-Arg-Phe-Lys-Gln-Asp-Asp-Gly-Trp-Ser-Pro-Trp-Ser-Glu-Trp (SEQ ID NO: 10.

12. The peptide of claim 11 consisting of SEQ ID NO: 10.

13. The peptide of claim 1, wherein the peptide modulates TGF-BI and/or MMP-9 activity through protein-protein interaction.

14. A composition comprising the peptide of claim 1, wherein the composition is prepared for administration to animals, or as a pharmaceutical formulation for administration to humans.

15. A method for stabilizing an atherosclerotic plaque and decreasing occurrence of plaque rupture events, the method comprising administering to an animal in need thereof a composition or pharmaceutical formulation comprising the peptide of claim 1.

* * * * *

SEQUENCE LISTING

```
<160> NUMBER OF SEQ ID NOS: 21

<210> SEQ ID NO 1
<211> LENGTH: 71
<212> TYPE: PRT
<213> ORGANISM: Artificial Sequence
<220> FEATURE:
<223> OTHER INFORMATION: Synthetic construct

<400> SEQUENCE: 1

Ser Ala Asp Asp Gly Trp Ser Pro Trp Ser Glu Trp Thr Ser Cys Ser
1               5                   10                  15

Thr Ser Cys Gly Asn Gly Ile Gln Gln Arg Gly Arg Ser Cys Asp Ser
            20                  25                  30

Leu Asn Asn Arg Cys Glu Gly Ser Ser Val Gln Thr Arg Thr Cys His
        35                  40                  45

Ile Gln Glu Cys Asp Lys Arg Phe Lys Gln Asp Gly Gly Trp Ser His
    50                  55                  60

Trp Ser Pro Trp Ser Ser Cys
65                  70


<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Lys Arg Phe Lys
1


<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Asp Asp Gly Trp
1


<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Asp Gly Gly Trp
1
```

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: X can be any amino acid

<400> SEQUENCE: 5

Asp Xaa Gly Trp
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Ala Asp Gly Trp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: X can be D or E
<220> FEATURE:
<221> NAME/KEY: misc_feature
<222> LOCATION: (3)..(3)
<223> OTHER INFORMATION: X can be G or L

<400> SEQUENCE: 7

Asp Xaa Xaa Trp
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Trp Ser Xaa Trp
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Trp Ser Pro Trp
1

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Lys Arg Phe Lys Gln Asp Asp Gly Trp Ser Pro Trp Ser Glu Trp
1 5 10 15

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: X can be any amino acid
<220> FEATURE:
<221> NAME/KEY: misc_feature
<222> LOCATION: (3)..(3)
<223> OTHER INFORMATION: X is L or G

<400> SEQUENCE: 11

Asp Xaa Xaa Trp
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: X is D or E
<220> FEATURE:
<221> NAME/KEY: misc_feature
<222> LOCATION: (2)..(2)
<223> OTHER INFORMATION: X is D or E
<220> FEATURE:
<221> NAME/KEY: misc_feature
<222> LOCATION: (3)..(3)
<223> OTHER INFORMATION: X is G or L

<400> SEQUENCE: 12

Xaa Xaa Xaa Trp
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Asp Glu Leu Trp
1

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct -continued
<220> FEATURE:
<221> NAME/KEY: misc_feature
<222> LOCATION: (3)..(3)
<223> OTHER INFORMATION: X is P or H
<220> FEATURE:
<221> NAME/KEY: misc_feature
<222> LOCATION: (6)..(6)
<223> OTHER INFORMATION: X is E or P

<400> SEQUENCE: 14

Trp Ser Xaa Trp Ser Xaa Trp
1               5

<210> SEQ ID NO 15
<211> LENGTH: 5
<212> TYPE: PRT
<213> ORGANISM: Artificial Seqeunce
<220> FEATURE:
<223> OTHER INFORMATION: Synthetic Construct

<400> SEQUENCE: 15

Lys Arg Phe Lys Gln
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Asp Gly Gly Trp Ser Pro Trp Ser Glu Trp
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: X is R or K
<220> FEATURE:
<221> NAME/KEY: misc_feature
<222> LOCATION: (2)..(2)
<223> OTHER INFORMATION: X is R or K
<220> FEATURE:
<221> NAME/KEY: misc_feature
<222> LOCATION: (3)..(3)
<223> OTHER INFORMATION: X is F, W or P
<220> FEATURE:
<221> NAME/KEY: misc_feature
<222> LOCATION: (4)..(4)
<223> OTHER INFORMATION: X is R or K
<220> FEATURE:
<221> NAME/KEY: misc_feature
<222> LOCATION: (5)..(5)
<223> OTHER INFORMATION: X is T, N or Q
<220> FEATURE:
<221> NAME/KEY: misc_feature
<222> LOCATION: (6)..(6)
<223> OTHER INFORMATION: X is D or E
<220> FEATURE:
<221> NAME/KEY: misc_feature
<222> LOCATION: (7)..(7)
<223> OTHER INFORMATION: X is D or E
<220> FEATURE:
<221> NAME/KEY: misc_feature
<222> LOCATION: (8)..(8)
<223> OTHER INFORMATION: X is G, S or C
<220> FEATURE:

```
<221> NAME/KEY: misc_feature
<222> LOCATION: (9)..(9)
<223> OTHER INFORMATION: X is F, W or P
<220> FEATURE:
<221> NAME/KEY: misc_feature
<222> LOCATION: (10)..(10)
<223> OTHER INFORMATION: X is G, S or C
<220> FEATURE:
<221> NAME/KEY: misc_feature
<222> LOCATION: (11)..(11)
<223> OTHER INFORMATION: X is F, W or P
<220> FEATURE:
<221> NAME/KEY: misc_feature
<222> LOCATION: (12)..(12)
<223> OTHER INFORMATION: X is F, W or P
<220> FEATURE:
<221> NAME/KEY: misc_feature
<222> LOCATION: (13)..(13)
<223> OTHER INFORMATION: X is G, S or C
<220> FEATURE:
<221> NAME/KEY: misc_feature
<222> LOCATION: (14)..(14)
<223> OTHER INFORMATION: X is D or E
<220> FEATURE:
<221> NAME/KEY: misc_feature
<222> LOCATION: (15)..(15)
<223> OTHER INFORMATION: X is F, W or P

<400> SEQUENCE: 17

Xaa Xaa Xaa Xaa Xaa Xaa Xaa Xaa Xaa Xaa Xaa Xaa Xaa Xaa Xaa
1               5                   10                  15


<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Asp Asp Gly Ala
1


<210> SEQ ID NO 19
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: X is any amino acid
<220> FEATURE:
<221> NAME/KEY: misc_feature
<222> LOCATION: (6)..(6)
<223> OTHER INFORMATION: X is P or H
<220> FEATURE:
<221> NAME/KEY: misc_feature
<222> LOCATION: (9)..(9)
<223> OTHER INFORMATION: X is E or P

<400> SEQUENCE: 19

Asp Xaa Gly Trp Ser Xaa Trp Ser Xaa Trp
1               5                   10


<210> SEQ ID NO 20
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (6)..(6)
<223> OTHER INFORMATION: X is D or E
<220> FEATURE:
<221> NAME/KEY: misc_feature
<222> LOCATION: (7)..(7)
<223> OTHER INFORMATION: X is any amino acid
<220> FEATURE:
<221> NAME/KEY: misc_feature
<222> LOCATION: (8)..(8)
<223> OTHER INFORMATION: X is G or L

<400> SEQUENCE: 20

Lys Arg Phe Lys Gln Xaa Xaa Xaa Trp
1               5


<210> SEQ ID NO 21
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: X is D or E
<220> FEATURE:
<221> NAME/KEY: misc_feature
<222> LOCATION: (2)..(2)
<223> OTHER INFORMATION: X is any amino acid
<220> FEATURE:
<221> NAME/KEY: misc_feature
<222> LOCATION: (3)..(3)
<223> OTHER INFORMATION: X is G or L
<220> FEATURE:
<221> NAME/KEY: misc_feature
<222> LOCATION: (6)..(6)
<223> OTHER INFORMATION: X is any amino acid
<220> FEATURE:
<221> NAME/KEY: misc_feature
<222> LOCATION: (9)..(9)
<223> OTHER INFORMATION: X is any amino acid

<400> SEQUENCE: 21

Xaa Xaa Xaa Trp Ser Xaa Trp Ser Xaa Trp
1               5                   10
```